US008975239B2

(12) United States Patent
Green et al.

(10) Patent No.: US 8,975,239 B2
(45) Date of Patent: *Mar. 10, 2015

(54) COMBINATIONS OF SAPACITABINE OR CNDAC WITH DNA METHYLTRANSFERASE INHIBITORS SUCH AS DECITABINE AND PROCAINE

(71) Applicant: Cyclacel Limited, London (GB)

(72) Inventors: Simon Richard Green, Dundee (GB); Ruth Mackay, Dundee (GB); Ian Neil Fleming, Angus (GB)

(73) Assignee: Cyclacel Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/960,489

(22) Filed: Aug. 6, 2013

(65) Prior Publication Data

US 2014/0100187 A1    Apr. 10, 2014

Related U.S. Application Data

(63) Continuation of application No. 12/997,197, filed as application No. PCT/GB2009/001418 on Jun. 5, 2009, now Pat. No. 8,530,445.

(30) Foreign Application Priority Data

Jun. 9, 2008 (GB) .................................. 0810552.0
Apr. 17, 2009 (GB) .................................. 0906696.0

(51) Int. Cl.
*A01N 43/04* (2006.01)
*A61K 31/70* (2006.01)
*A61K 31/405* (2006.01)
*A61K 31/245* (2006.01)
*A61K 31/353* (2006.01)
*A61K 31/502* (2006.01)
*A61K 31/706* (2006.01)
*A61K 31/7068* (2006.01)
*A61K 45/06* (2006.01)

(52) U.S. Cl.
CPC ............ *A61K 31/405* (2013.01); *A61K 31/245* (2013.01); *A61K 31/353* (2013.01); *A61K 31/502* (2013.01); *A61K 31/706* (2013.01); *A61K 31/7068* (2013.01); *A61K 45/06* (2013.01)
USPC .................................. 514/49; 514/42; 514/43

(58) Field of Classification Search
None
See application file for complete search history.

(56) References Cited

U.S. PATENT DOCUMENTS

| 5,616,567 | A  | 4/1997  | Sasaki et al. |
| 5,654,420 | A  | 8/1997  | Matsuda et al. |
| 5,691,319 | A  | 11/1997 | Kaneko et al. |
| 5,824,984 | A  | 10/1998 | Morrow |
| 6,369,086 | B1 | 4/2002  | Davis et al. |
| 6,462,063 | B1 | 10/2002 | Ho et al. |
| 6,908,906 | B2 | 6/2005  | Takita et al. |
| 2002/0156033 | A1 | 10/2002 | Bratzler et al. |
| 2002/0161377 | A1 | 10/2002 | Rabkin |
| 2002/0165569 | A1 | 11/2002 | Ramzipoor et al. |
| 2003/0026801 | A1 | 2/2003  | Weiner et al. |
| 2003/0087873 | A1 | 5/2003  | Stuyver et al. |
| 2003/0124512 | A1 | 7/2003  | Stuyver |
| 2003/0134827 | A1 | 7/2003  | Duan et al. |
| 2004/0097461 | A1 | 5/2004  | Sommadossi et al. |
| 2005/0009773 | A1 | 1/2005  | Kandimalla et al. |
| 2005/0014716 | A1 | 1/2005  | Wang et al. |
| 2005/0124532 | A1 | 6/2005  | Sommadossi et al. |
| 2005/0171096 | A1 | 8/2005  | Sheppeck et al. |
| 2006/0211369 | A1 | 9/2006  | Steelberg et al. |
| 2011/0028421 | A1 | 2/2011  | Engel et al. |

FOREIGN PATENT DOCUMENTS

| CN | 101185629 | 5/2008 |
| DE | 7304511 | 2/1974 |
| DE | 2305815 | 8/1974 |
| DE | 4419792 C1 | 2/1996 |
| EP | 0535231 B1 | 4/1993 |
| EP | 0536936 A1 | 4/1993 |
| EP | 1364959 B1 | 11/2003 |

(Continued)

OTHER PUBLICATIONS

Accession No. 2000-565332, Hanaoka, K. et al., "Antitumor liposome preparations comprise sterol compound, phosphatidylcholine compound and 1-(2'-cyano-2'-deoxy-beta-arabino-pentofuranosyl) cytosine," (2000).

Accession No. 2001-040935, Hanaoka, K. et al., "Liposome preparation with high drug transfer contains 1-(2-C-cyano-2-deoxy-beta-D-arabinopentofuranosyl)-N4-palmitoyl cytosine antitumor agent," (2001).

Bellone, Graziella et al., "Antagonistic Interactions Between Gemcitabine and 5-Fluorouracil in the Human Pancreatic Carcinoma Cell Line Capan-2," Cancer Biology & Therapy, vol. 5(10):1294-1303 (2006).

Berge, Stephen M. et al., "Pharmaceutical Salts," Journal of Pharmaceutical Sciences, vol. 66(1):1-19 (1977).

(Continued)

*Primary Examiner* — Patrick Lewis
(74) *Attorney, Agent, or Firm* — Nelson Mullins Riley & Scarborough LLP; Cynthia L. Kanik; Adam J. Gastonguay

(57) ABSTRACT

A first aspect of the invention relates to a combination comprising a DNA methyltransferase inhibitor and 1-(2-C-cyano-2-dioxy-β-D-arabino-pentofuranosyl)-N4-palmitoyl cytosine, or a metabolite thereof. A second aspect of the invention relates to a pharmaceutical product comprising a DNA methyltransferase inhibitor and 1-(2-C-cyano-2-dioxy-β-D-arabino-pentofuranosyl)-N4-palmitoyl cytosine, or a metabolite thereof, as a combined preparation for simultaneous, sequential or separate use in therapy. A third aspect of the invention relates to a method of treating a proliferative disorder, said method comprising simultaneously, sequentially or separately administering a DNA methyltransferase inhibitor and 1-(2-C-cyano-2-dioxy-β-D-arabino-pentofuranosyl)-N4-palmitoyl cytosine, or a metabolite thereof, to a subject.

15 Claims, 3 Drawing Sheets

(56) References Cited

FOREIGN PATENT DOCUMENTS

Figure 1A:
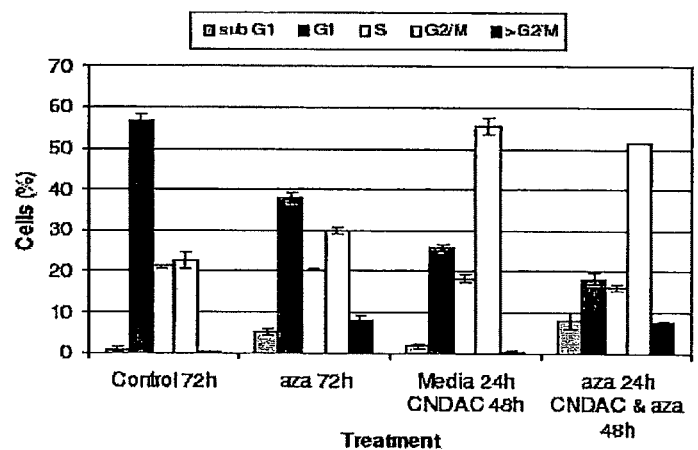

| | | |
|---|---|---|
| EP | 1669364 A2 | 6/2006 |
| EP | 1736478 A1 | 12/2006 |
| JP | 2007-513132 | 5/2007 |
| WO | 97/11647 A1 | 4/1997 |
| WO | 01/97843 A2 | 12/2001 |
| WO | 02/28829 A2 | 4/2002 |
| WO | 02/32920 A2 | 4/2002 |
| WO | 02/46182 A1 | 6/2002 |
| WO | 02/064609 A1 | 8/2002 |
| WO | 03/039536 A1 | 5/2003 |
| WO | 2004/091441 A2 | 10/2004 |
| WO | 2004/103301 A2 | 12/2004 |
| WO | 2005/000204 A2 | 1/2005 |
| WO | 2005/053699 A1 | 6/2005 |
| WO | 2006/090931 A1 | 8/2006 |
| WO | 2007/054731 A1 | 5/2007 |
| WO | 2007/072061 A2 | 6/2007 |
| WO | 2007/132228 A1 | 11/2007 |
| WO | 2008/007113 A2 | 1/2008 |

OTHER PUBLICATIONS

Bible, Keith C. et al., "Cytotoxic Synerty between Flavopiridol (NSC 649890, L86-8275) and Various Antineoplastic Agents: The Importance of Sequence of Administration," Cancer Research, vol. 57:3375-3380 (1997).

Burch, P.A. et al., "Phase I Study of Orally Administered CS-682 in Solid Tumors," Proceedings of ASCO, vol. 20:92a, Poster No. 364 (2001).

CAplus, Accession No. 136:310184, Chong, Lee et al., "Preparation of hydroxamic acid peptide deformylase inhibitors as antibacterial agents," (2011).

Chou, Ting-Chao et al., "Quantitative Analysis of Dose-effect Relationships: The Combined Efforts of Multiple Drugs or Enzyme Inhibitors," Adv. Enzyme Requl., vol. 22:27-55 (1984).

Danesi, Romano et al., "Pharmacogenetic determinants of anti-cancer drug activity and toxicity," Trends in Pharmacological Science, vol. 22*8):420-426 (2001).

Delaunoit, Thierry et al., "A phase I clinical and pharmacokinetic study of CS-682 administered orally in advanced malignant solid tumors," Investigational New Drugs, vol. 24:327-333 (2006).

De Vos, Dick et al., "Decitabine: a historical review of the development of an epigenetic drug," Ann. Hematol., vol. 84:3-8 (2005).

Donehower, Ross et al., "A Phase I Study of CS-682, an Oral Antimetabolite, in Patients with Refractory Solid Tumors," 2000 ASCO Meeting, Proc. Am. Soc. Clin. Oncol., vol. 19, Abstract No. 764 (2000).

Fenaux, Pierre, "Inhibitors of DNA methylation: beyond myelodysplastic syndromes," Nature Clinical Practice Oncology, vol. 2:S36-S44 (2005).

Fujita, F. et al., "Antitumor activity of a novel nucleoside 1-(2-C-cyano-2-deoxy-beta-D-arabino-pentofuranosy)-N4-palmitoylcytosine (CS-682)," Proceedings of the American Association for Cancer Research, 88th Annual Meeting, vol. 38:101-102, Abstract No. 681 (1997).

Gilbert, Jill et al., "A Phase I study of the oral antimetabolite, CS-682, administered once daily 5 days per week in patients with refractory solid tumor malignancies," Invest. New Drugs, vol. 24:499-508 (2006).

Green, Simon R. et al., "Synergistic Interactions Between Sapacitabine (CYC682) and Inhibitors of Either Histone Deacetylase of Methyltransferase in Acute Myeloid Leukemia Cell Lines," 100th Annual Meeting of the American Association for Cancer Research, Abstract No. 4552, 1 page (2009).

Hanaoka, K. et al., "A novel mechanism of action of a new antitumor nucleoside 1-(2-C-cyano-2-deoxy-beta-D-arabino-pentofuranosyl)-N4-Palmitoylcytosine (CS-682)," Proceedings of the American Association for Cancer Research, 88th Annual Meeting, vol. 38:101, Abstract No. 680 (1997).

Hanaoka, Kenji et al., "Antitumor Activity and Novel DNA-Self-Strand-Breaking Mechanism of CNDAC (1-(2-C-cyano-2-deoxy-b-D-arabino-pentofuranosyl) cytosine) and its N4-Palmitoyl Derivative (CS-682)," Int. J. Cancer, vol. 82:226-236 (1999).

Kaneko, M. et al., "Synthesis and antitumor activity of a novel anti-tumor nucleoside 1-(2-C-cyano-2-deoxy-beta-D-arabino-pentofuranosyl)-N4-palmitoylcytosine (CS-682)," Proceedings of the American Association for Cancer Research, 88th Annual Meeting, vol. 38:101, Abstract No. 679 (1997).

Kong, Xiang-Bin et al., "Induction of Deoxycytidine Kinase by 5-Azacytidine in an HL-60 Cell Line Resistant to Arabinosylcytosine," Molecular Pharmacology, vol. 39:250-257 (1990).

List, A. et al., "Developmental therapeutics for MDS," Leukemia Research, vol. 33:S27-S28 (2009).

Miyamoto, K. et al., "DNA methylation and cancer—DNA methylation as a target of cancer chemotherapy," Cancer and Chemotherapy, vol. 30(13):2021-2029 (2003).

Peckham, Michael et al., "Biological and Pharmacological Basis of Chemotherapy, Biological Basis," Oxford Textbook of Oncology, vol. 1, Oxford University Press, Oxford, England, pp. 447-453 (1995).

Qin, Taichun et al., "Effect of Cytarabine and Decitabine in Combination in Human Leukemic Cell Lines," Clin Cancer Res., vol. 13(14):4225-4232 (2007).

Sankyo Co., Ltd., "CS-682," Drugs of the Future, vol. 24(9):957-960 (1999).

Serova, M. et al., "Antiproliferative effects of sapacitabine (CYC682), a novel 2'-deoxycytidine-derivative in human cancer cells," British Journal of Cancer, vol. 97:628-636 (2007).

Silverman, Richard B., "Drug Discovery, Design, and Development," The Organic Chemistry of Drug Design and Drug Action, Academic Press, San Diego, Chapter 2, pp. 4-47 (1992).

STN Gen Caesar Accession No. 1364, "Cyclacel's cancer drug starts Phase II testing," (2002).

STN Database Descriptions, "Rapra," 2006 Chemical Abstracts Catalog, Chemical Abstracts Service, p. 52 (2006).

Stresemann, Carlo et al., "Functional Diversity of DNA Methyltransferase Inhibitors in Human Cancer Cell Lines," Cancer Res., vol. 66(5):2794-2800 (2006).

The Merck Manual of Diagnosis and Therapy, Seventeenth Edition, Mark H. Beers (Ed.), Merck Research Laboratories, Whitehouse Station, N.J., pp. 397-398, 948-949, 1916 and 1979-1981 (1999).

Tolcher, A. et al., "Phase I study of sapacitabine, an oral nucleoside analogue, in patients with refractory solid tumors or lymphomas," European Journal of Cancer, Supplement, vol. 4(12):142, Poster No. 463 (2006).

Vippagunta, Sudha R. et al., "Crystalline solids," Advanced Drug Delivery Reviews, vol. 48:3-26 (2001).

Whittaker, Mark et al., "Design and Therapeutic Application of Matrix Metalloproteinase Inhibitors," Chem. Rev., vol. 99:2735-2776 (1999).

Whittaker, Mark et al., "MMP-12 inhibitors, AstraZeneca: WO2004020415," Expert Opin. Ther. Patents, vol. 14 (11):1637-1640 (2004).

Wu, Ming et al., "High-Resolution Magnetic Resonance Imaging of the Efficacy of the Cytosine Analogue 1-[2-C-Cyano-2-deoxy-b-D-arabino-pentofuranosyl]-N4-palmitoyl Cytosine (CS-682) in a Liver-Metastasis Athymic Nude Mouse Mode," Cancer Research, vol. 63:2477-2482 (2003).

International Preliminary Report on Patentability for Application No. PCT/GB2006/004230, 8 pages, dated May 14, 2008.

International Search Report for Application No. PCT/GB2006/004230, 4 pages, dated Feb. 5, 2007.

Written Opinion for Application No. PCT/GB2004/005081, 6 pages, dated Jun. 7, 2006.

COMBINATIONS OF SAPACITABINE OR CNDAC WITH DNA METHYLTRANSFERASE INHIBITORS SUCH AS DECITABINE AND PROCAINE

FIELD OF THE INVENTION

The present invention relates to a pharmaceutical combination suitable for the treatment of cancer and other proliferative disorders.

BACKGROUND TO THE INVENTION

DNA methyltransferases are a family of enzymes that promote the covalent addition of a methyl group to a specific nucleotide base in a molecule of DNA. All the known DNA methyltransferases use S-adenosyl methionine (SAM) as the methyl donor. Four active DNA methyltransferases have been identified in mammals. They are named DNMT1, DNMT2, DNMT3A and DNMT3B.

DNMT1 is the most abundant DNA methyltransferase in mammalian cells and considered to be the key maintenance methyltransferase in mammals. It predominantly methylates hemimethylated CpG di-nucleotides in the mammalian genome and is responsible for maintaining methylation patterns established in development. The enzyme is about 1620 amino acids long, the first 1100 amino acids constituting the regulatory domain, and the remaining residues constituting the catalytic domain. These are joined by Gly-Lys repeats. Both domains are required for the catalytic function of DNMT1. DNMT3 is a family of DNA methyltransferases that can methylate hemimethylated and unmethylated CpG at the same rate. The architecture of DNMT3 enzymes is similar to DNMT1 with a regulatory region attached to a catalytic domain.

Recent work has revealed how DNA methylation and chromatin structure are linked at the molecular level and how methylation anomalies play a direct causal role in tumorigenesis and genetic disease. Much new information has also come to light regarding DNA methyltransferases, in terms of their role in mammalian development and the types of proteins they are known to interact with. Rather than enzymes that act in isolation to copy methylation patterns after replication, the types of interactions discovered thus far indicate that DNA methyltransferases may be components of larger complexes actively involved in transcriptional control and chromatin structure modulation. These findings should enhance the understanding of the myriad roles of DNA methylation in disease, as well as leading to novel therapies for preventing or repairing these defects.

It is well established in the art that active pharmaceutical agents can often be given in combination in order to optimise the treatment regime. The present invention therefore seeks to provide a new combination of known pharmaceutical agents that is particularly suitable for the treatment of proliferative disorders, especially cancer. More specifically, the invention centres on the surprising and unexpected effects associated with using certain pharmaceutical agents in combination.

STATEMENT OF INVENTION

In a first aspect, the invention provides a combination comprising a DNA methyltransferase inhibitor and 1-(2-C-cyano-2-dioxy-β-D-arabino-pentofuranosyl)-N4-palmitoyl cytosine (also known as "CYC682" or sapacitabine), or a metabolite thereof.

Qin T et al (2007, 13, Clin. Cancer Res. 4225-4232) disclose the effect of combinations of cytarabine and decitabine in various human leukemic cell lines. Likewise, Kong X B et al (1991, Molecular Pharmacol. 39, 250-257) suggest that 5-azacitidine causes upregulation of dCK in a cell line that is resistant to cytarabine, resulting in a decrease in the $IC_{50}$ value for cytarabine from 12.5 to 0.55 µM. However, to date there are no teachings on the use of DNA methyltransferase inhibitors in combination with sapacitabine, which has a unique mode of action over other nucleoside metabolites.

A second aspect provides a pharmaceutical composition comprising a combination according to the invention admixed with a pharmaceutically acceptable carrier, diluent or excipient.

A third aspect relates to the use of a combination according to the invention in the preparation of a medicament for treating a proliferative disorder.

A fourth aspect relates to a pharmaceutical product comprising a DNA methyltransferase inhibitor and 1-(2-C-cyano-2-dioxy-β-D-arabino-pentofuranosyl)-N4-palmitoyl cytosine, or a metabolite thereof, as a combined preparation for simultaneous, sequential or separate use in therapy A fifth aspect relates to a method of treating a proliferative disorder, said method comprising simultaneously, sequentially or separately administering a DNA methyltransferase inhibitor and 1-(2-C-cyano-2-dioxy-β-D-arabino-pentofuranosyl)-N4-palmitoyl cytosine, or a metabolite thereof, to a subject.

A sixth aspect relates to the use of a DNA methyltransferase inhibitor in the preparation of a medicament for the treatment of a proliferative disorder, wherein said treatment comprises simultaneously, sequentially or separately administering a DNA methyltransferase inhibitor and 1-(2-C-cyano-2-dioxy-β-D-arabino-pentofuranosyl)-N4-palmitoyl cytosine, or a metabolite thereof, to a subject.

A seventh aspect relates to the use of a DNA methyltransferase inhibitor and 1-(2-C-cyano-2-dioxy-β-D-arabino-pentofuranosyl)-N4-palmitoyl cytosine, or a metabolite thereof, in the preparation of a medicament for treating a proliferative disorder.

An eighth aspect relates to the use of a DNA methyltransferase inhibitor in the preparation of a medicament for the treatment of a proliferative disorder, wherein said medicament is for use in combination therapy with 1-(2-C-cyano-2-dioxy-β-D-arabino-pentofuranosyl)-N4-palmitoyl cytosine, or a metabolite thereof.

A ninth aspect relates to the use of 1-(2-C-cyano-2-dioxy-β-D-arabino-pentofuranosyl)-N4-palmitoyl cytosine, or a metabolite thereof, in the preparation of a medicament for the treatment of a proliferative disorder, wherein said medicament is for use in combination therapy with a DNA methyltransferase inhibitor.

A tenth aspect of the invention relates to a combination as described above for the treatment of a proliferative disorder.

DETAILED DESCRIPTION

The effect of drug combinations is inherently unpredictable and there is often a propensity for one drug to partially or completely inhibit the effects of the other. The present invention is based on the surprising observation that administering 1-(2-C-cyano-2-dioxy-β-D-arabino-pentofuranosyl)-N4-palmitoyl cytosine and a DNA methyltransferase inhibitor in combination, either simultaneously, separately or sequentially, does not lead to any adverse interaction between the two agents. The unexpected absence of any such antagonistic interaction is critical for clinical applications.

In a preferred embodiment, the combination of 1-(2-C-cyano-2-dioxy-β-D-arabino-pentofuranosyl)-N4-palmitoyl cytosine and DNA methyltransferase inhibitor produces an enhanced effect as compared to either drug administered alone. The surprising nature of this observation is in contrast to that expected on the basis of the prior art.

The preferred embodiments as set out below are applicable to all the above-mentioned aspects of the invention.

1-(2-C-cyano-2-dioxy-β-D-arabino-pentofuranosyl)-$N^4$-palmitoyl cytosine (I), also known as 2'-cyano-2-deoxy-$N^4$-palmitoyl-1-β-D-arabinofuranosylcytosine (Hariaoka, K., et al, *Int. J. Cancer,* 1999:82:226-236; Donehower R, et al, *Proc Am Soc Clin Oncol,* 2000: abstract 764; Burch, P A, et al, *Proc Am Soc Clin Oncol,* 2001: abstract 364), is an orally administered novel 2'-deoxycytidine antimetabolite prodrug of the nucleoside CNDAC, 1-(2-C-Cyano-2-deoxy-β-D-arabino-pentafuranosyl)-cytosine.

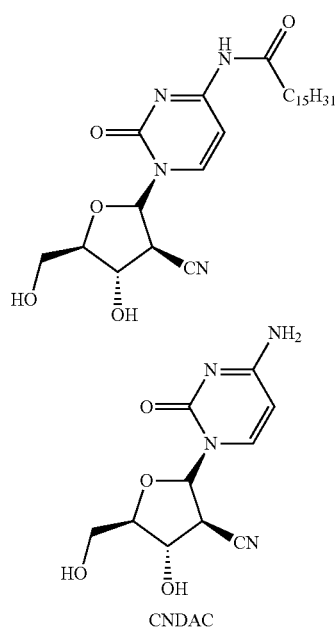

CNDAC 1-(2-C-cyano-2-dioxy-β-D-arabino-pentofuranosyl)-$N^4$-palmitoyl cytosine (I) (also known as "CYC682" or sapacitabine) has a unique mode of action over other nucleoside metabolites such as gemcitabine in that it has a spontaneous DNA strand breaking action, resulting in potent anti-tumour activity in a variety of cell lines, xenograft and metastatic cancer model.

1-(2-C-cyano-2-dioxy-β-D-arabino-pentofuranosyl)-$N^4$-palmitoyl cytosine (I) has been the focus of a number of studies in view of its oral bioavailability and its improved activity over gemcitabine (the leading marketed nucleoside analogue) and 5-FU (a widely-used antimetabolite drug) based on preclinical data in solid tumours. Recently, investigators reported that (I) exhibited strong anticancer activity in a model of colon cancer. In the same model, (I) was found to be superior to either gemcitabine or 5-FU in terms of increasing survival and also preventing the spread of colon cancer metastases to the liver (Wu M, et al, *Cancer Research,* 2003: 63:2477-2482). To date, phase I data from patients with a variety of cancers suggest that (I) is well tolerated in humans, with myelosuppression as the dose limiting toxicity.

In one preferred embodiment, the DNA methyltransferase inhibitor is a cytosine analogue. More preferably, the DNA methyltransferase inhibitor is selected from azacitidine, decitabine and zebularine.

Azacitidine (vidaza; 5-azacitidine) and decitabine (dacogen; 5-aza-2'-deoxycytidine) were the first DNA methyltransferase (DNMT) inhibitors to be described. In cells, azacitidine can be converted to decitabine by the enzyme ribonucleotide reductase. These pyrimidine analogues of cytidine incorporate into RNA and DNA respectively, and form covalent complexes with DNMTs, leading to depletion of active enzymes (Fenaux P, (2005) Nature Clinical Practice, 2, S36-44). Azacitidine also incorporates into RNA, giving rise to defective messenger and transfer RNA, ultimately resulting in inhibition of protein synthesis. Aside from methyltransferase inhibition, these agents are cytotoxic at higher doses, because they directly interfere with DNA synthesis.

In one highly preferred embodiment, the DNA methyltransferase inhibitor is decitabine.

Decitabine or 5-aza-2'-deoxycytidine (trade name Dacogen) is the compound 4-amino-1-(2-deoxy-b-D-erythro-pentofuranosyl)-1,3,5-triazin-2(1H)-one, the structure of which is shown below.

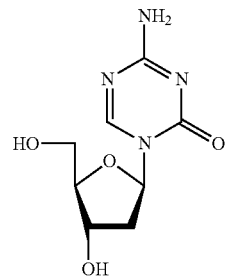

Decitabine is indicated for the treatment of myelodysplastic syndromes (MDS) including previously treated and untreated, de novo and secondary MDS of all French-American-British subtypes (refractory anemia, refractory anemia with ringed sideroblasts, refractory anemia with excess blasts, refractory anemia with excess blasts in transformation, and chronic myelomonocytic leukemia) and Intermediate-1, Intermediate-2, and High-Risk International Prognostic Scoring System groups.

Decitabine is believed to exert its antineoplastic effects after phosphorylation and direct incorporation into DNA. Decitabine inhibits DNA methyltransferase, causing hypomethylation of DNA and cellular differentiation or apoptosis. Decitabine-induced hypomethylation in neoplastic cells may restore normal function to genes that are critical for the control of cellular differentiation and proliferation. In rapidly dividing cells, the cytotoxicity of decitabine may also be attributed to the formation of covalent adducts between DNA methyltransferase and compound that has been incorporated into DNA. Non-proliferating cells are relatively insensitive to decitabine.

In another highly preferred embodiment, the DNA methyltransferase inhibitor is azacitidine (trade name Vidaza) is the compound 4-amino-1-β-D-ribofuranosyl-s-triazin-2 (1H)-one, the structure of which is shown below.

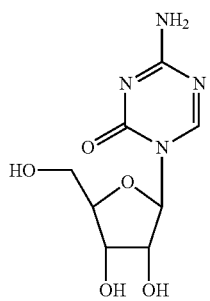 [SMILES: Nc1ncn(C2OC(CO)C(O)C2O)c(=O)n1]

Azacitidine is an anti-neoplastic pyrimidine nucleoside analog used to treat several subtypes of myelodysplastic syndrome, diseases caused by abnormalities in the blood-forming cells of the bone marrow which result in underproduction of healthy blood cells. The drug exerts a cytotoxic effect on rapidly dividing cells, including cancerous cells, and may help restore normal function to genes controlling proper cellular differentiation and proliferation.

Azacitidine is specifically indicated for the treatment of the following myelodysplastic syndrome subtypes: refractory anemia, refractory anemia with ringed sideroblasts (if accompanied by neutropenia or thrombocytopenia or requiring transfusions), refractory anemia with excess blasts, refractory anemia with excess blasts in transformation and chronic myelomonocytic leukemia.

Azacitidine is believed to exert its antineoplastic effects by causing hypomethylation of DNA and direct cytotoxicity on abnormal haematopoietic cells in the bone marrow. The concentration of azacitidine required for maximum inhibition of DNA methylation in vitro does not cause major suppression of DNA synthesis. Hypomethylation may restore function to genes that are critical for differentiation or proliferation. The cytotoxic effects of azacitidine cause the death of rapidly dividing cells, including cancer cells that are no longer responsive to normal growth control mechanisms. Non-proliferating cells are relatively insensitive to azacitidine.

In another highly preferred embodiment, the DNA methyltransferase inhibitor is zebularine, also known as 1-(β-D-ribofuranosyl)-1,2-dihydropyrimidin-2-one or 2-pyrimidone-1-β-D-riboside, the structure of which is shown below.

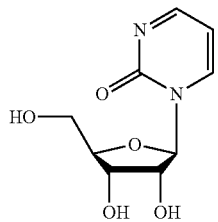

In another preferred embodiment, the DNA methyltransferase inhibitor is a non-nucleoside analogue. More preferably, the DNA methyltransferase inhibitor is selected from procainamide, procaine, hydralazine and ((−)-epigallocatechin-3-gallate (EGCG).

Procainamide (trade names Pronestyl, Procan, Procanbid) is the compound 4-amino-N-(2-diethylaminoethyl)benzamide, the structure of which is shown below.

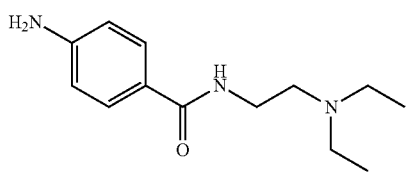 [SMILES: CCN(CC)CCNC(=O)c1ccc(N)cc1]

Procainamide has been shown to inhibit DNA methyltransferase activity and reactivate silenced gene expression in cancer cells by reversing CpG island hypermethylation. Procainamide specifically inhibits the hemimethylase activity of DNA methyltransferase 1 (DNMT1), the mammalian enzyme thought to be responsible for maintaining DNA methylation patterns during replication.

Procaine is the compound 2-(diethylamino)ethyl-4-aminobenzoate, the structure of which is shown below.

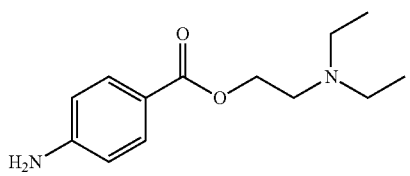 [SMILES: CCN(CC)CCOC(=O)c1ccc(N)cc1]

Procaine is a DNA-demethylating agent that is understood to inhibit DNA methyltransferases by interfering with enzyme activity.

Hydralazine (Apresoline) is the compound 1-hydrazinophthalazine monohydrochloride, the structure of which is shown below.

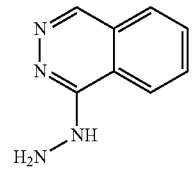

((−)-Epigallocatechin-3-gallate (EGCG) is a catechin analogue having the structure shown below.

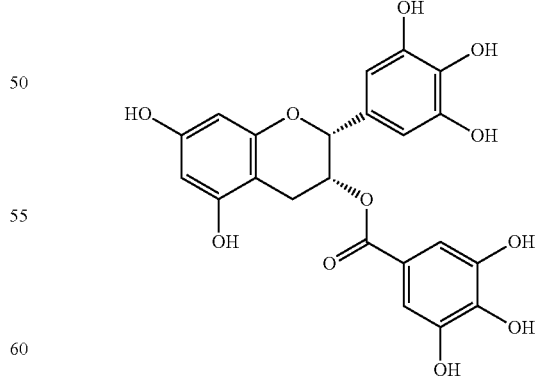

EGCG is understood to inhibit DNMT activity and reactivate methylation-silenced genes in cancer cells.

In another preferred embodiment, the DNA methyltransferase inhibitor is RG108, also known as N-phthalyl-1-tryptophan, the structure of which is shown below.

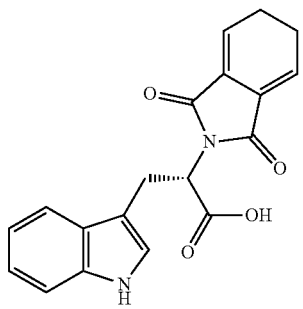 [SMILES: O=C(O)[C@H](Cc1c[nH]c2ccccc12)N1C(=O)C2=CCCC=C2C1=O]

RG108 is a DNA methyltransferase inhibitor that is understood to inhibit DNA methyltransferases by interfering with enzyme activity. In particular, RG108 is believed to reactivate tumor suppressor gene expression (p16, SFRP1, secreted frizzled related protein-1, and TIMP-3) in tumor cells by DNA demethylation. RG108 also inhibits human tumor cell line (HCT116, NALM-6) proliferation and increases doubling time in culture.

The term "proliferative disorder" is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, anti-parasitic disorders such as malaria, emphysema and alopecia. In these disorders, the compounds of the present invention may induce apoptosis or maintain stasis within the desired cells as required.

Preferably, the proliferative disorder is a cancer or leukaemia, most preferably selected from lung cancer, prostate cancer, bladder cancer, head and neck cancer, colon cancer, breast cancer, renal cancer, gastric cancer, hepatic cancer, sarcoma, lymphoma, cutaneous T-cell lymphoma and multiple myeloma.

In one especially preferred embodiment, the proliferative disorder is a haematological malignancy, for example, advanced leukemias or myelodysplastic syndromes (MDS). Other examples include acute myelogenous leukemia (AML), acute lymphocytic leukemia (ALL) or chronic lymphocytic leukemia (CLL).

In one particularly preferred embodiment, the proliferative disorder is selected from lung cancer, lymphoblastic leukaemia and acute myelogenous leukaemia.

As used herein the phrase "preparation of a medicament" includes the use of the components of the invention directly as the medicament in addition to their use in any stage of the preparation of such a medicament.

As used herein, the term "combination therapy" refers to therapy in which the sapacitabine, or metabolite thereof, and DNA methyltransferase inhibitor are administered, if not simultaneously, then sequentially within a timeframe that they both are available to act therapeutically within the same time-frame.

The sapacitabine, or metabolite thereof, and DNA methyltransferase inhibitor may be administered simultaneously, in combination, sequentially or separately (as part of a dosing regime).

As used herein, "simultaneously" is used to mean that the two agents are administered concurrently, whereas the term "in combination" is used to mean they are administered, if not simultaneously, then "sequentially" within a timeframe that they both are available to act therapeutically within the same time-frame. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction therebetween, and their respective half-lives.

In contrast to "in combination" or "sequentially", "separately" is used herein to mean that the gap between administering one agent and the other is significant i.e. the first administered agent may no longer be present in the bloodstream in a therapeutically effective amount when the second agent is administered.

In one preferred embodiment of the invention, the DNA methyltransferase inhibitor is administered sequentially or separately prior to the 1-(2-C-cyano-2-dioxy-β-D-arabino-pentofuranosyl)-N4-palmitoyl cytosine. Preferably, the DNA methyltransferase inhibitor is administered at least 4 hours before the 1-(2-C-cyano-2-dioxy-β-D-arabino-pentofuranosyl)-N4-palmitoyl cytosine, and more preferably at least 72 hours before the 1-(2-C-cyano-2-dioxy-β-D-arabino-pentofuranosyl)-N4-palmitoyl cytosine.

In a particularly preferred embodiment, the 1-(2-C-cyano-2-dioxy-β-D-arabino-pentofuranosyl)-N4-palmitoyl cytosine is administered sequentially or separately prior to the DNA methyltransferase inhibitor. Preferably, the 1-(2-C-cyano-2-dioxy-β-D-arabino-pentofuranosyl)-N4-palmitoyl cytosine is administered at least one hour before the DNA methyltransferase inhibitor, and more preferably at least 24 hours before the DNA methyltransferase inhibitor.

In one preferred embodiment, the DNA methyltransferase inhibitor and 1-(2-C-cyano-2-dioxy-β-D-arabino-pentofuranosyl)-N4-palmitoyl cytosine are each administered in a therapeutically effective amount with respect to the individual components; in other words, the DNA methyltransferase inhibitor and 1-(2-C-cyano-2-dioxy-β-D-arabino-pentofuranosyl)-N4-palmitoyl cytosine are administered in amounts that would be therapeutically effective even if the components were administered other than in combination.

In another preferred embodiment, the DNA methyltransferase inhibitor and 1-(2-C-cyano-2-dioxy-β-D-arabino-pentofuranosyl)-N4-palmitoyl cytosine are each administered in a sub-therapeutic amount with respect to the individual components; in other words, the DNA methyltransferase inhibitor and 1-(2-C-cyano-2-dioxy-β-D-arabino-pentofuranosyl)-N4-palmitoyl cytosine are administered in amounts that would be therapeutically ineffective if the components were administered other than in combination.

Preferably, the 1-(2-C-cyano-2-dioxy-β-D-arabino-pentofuranosyl)-N4-palmitoyl cytosine and DNA methyltransferase inhibitor interact in a synergistic manner. As used herein, the term "synergistic" means that 1-(2-C-cyano-2-dioxy-β-D-arabino-pentofuranosyl)-N4-palmitoyl cytosine and the DNA methyltransferase inhibitor produce a greater effect when used in combination than would be expected from adding the individual effects of the two components. Advantageously, a synergistic interaction may allow for lower doses of each component to be administered to a patient, thereby decreasing the toxicity of chemotherapy, whilst producing and/or maintaining the same therapeutic effect. Thus, in a particularly preferred embodiment, each component can be administered in a sub-therapeutic amount.

Metabolite

As used herein, the term "metabolite" encompasses chemically modified entities that are produced by metabolism of 1-(2-C-cyano-2-dioxy-β-D-arabino-pentofuranosyl)-N4-palmitoyl cytosine.

In one particularly preferred embodiment of the invention, the metabolite of 1-(2-C-cyano-2-dioxy-β-D-arabino-pentofuranosyl)-N4-palmitoyl cytosine is 2'-C'-cyano-2'-dioxy-1-β-D-arabino-pentofuranosyl cytosine (CNDAC).

In one highly preferred embodiment, the metabolite of sapacitabine is CNDAC and the DNA methyltransferase is decitabine. For this embodiment, the components of the combination may be administered simultaneously, sequentially or separately. Preferably, the components are administered sequentially or separately (e.g. pre-treatment with CNDAC or decitabine).

In another highly preferred embodiment, the metabolite of sapacitabine is CNDAC and the DNA methyltransferase is azacitidine. Preferably, for this particular embodiment, the components of the combination are administered sequentially or separately, pretreatment with azacitidine being particularly preferred.

In another particularly preferred embodiment of the invention, 1-(2-C-cyano-2-dioxy-β-D-arabino-pentofuranosyl)-N4-palmitoyl cytosine is metabolized intracellularly to the active metabolite CNDAC-triphosphate (CNDACTP), a process involving both the cleavage of the palmitoyl moiety and activation to CNDACTP by the action of nucleoside kinases.

Salts/Esters

The agents of the present invention can be present as salts or esters, in particular pharmaceutically acceptable salts or esters.

Pharmaceutically acceptable salts of the agents of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

The invention also includes where appropriate all enantiomers and tautomers of the agents. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e.; $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the agents of the present invention. The terms used in the claims encompass these forms.

Polymorphs

The invention furthermore relates to agents of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes agents of the present invention in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 2000 mg and more preferably from 50-1000 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-500 mg, of active ingredient per dose.

Compositions may be formulated in unit dosage form, i.e., in the form of discrete portions containing a unit dose, or a multiple or sub-unit of a unit dose.

In a particularly preferred embodiment, the combination or pharmaceutical composition of the invention is administered intravenously.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.1 to 30 mg/kg body weight, such as from 2 to 20 mg/kg, more preferably from 0.1 to 1 mg/kg body weight.

By way of guidance, 1-(2-C-cyano-2-dioxy-β-D-arabino-pentofuranosyl)-N4-palmitoyl cytosine is typically administered in accordance with a physician's direction at dosages between 1 and 120 mg/m$^2$ body surface. Preferably, the dose is administered orally. The doses can be given 5 days a week for 4 weeks, or 3 days a week for 4 weeks. Dosages and frequency of application are typically adapted to the general medical condition of the patient and to the severity of the adverse effects caused, in particular to those caused to the hematopoietic, hepatic and to the renal system. The total daily dose can be administered as a single dose or divided into separate dosages administered two, three or four time a day.

The DNA methyltransferase inhibitor is typically administered subcutaneously or intravenously in accordance with a physician's direction. By way of guidance, the recommended decitabine dose is 15 mg/m$^2$ administered by continuous intravenous infusion over 3 h repeated every 8 h for 3 days (decitabine clinical label; Fenaux P. (2005) Nature Clinical Practice, 2, S36-44). This cycle is preferably repeated every 6 weeks. Patients with advanced solid tumours typically receive a 72 h infusion of decitabine at 20-30 mg/m$^2$/day. By way of guidance, the recommended starting dose of azacitidine is 75 mg/m$^2$ subcutaneously or intravenously, daily for 7 days (azacitidine clinical label; Fenaux P. (2005) Nature Clinical Practice, 2, S36-44).

The present invention is further described by way of example, and with reference the following Figures, wherein:

FIG. 1 shows the effect of azacitidine in combination with CNDAC on the cell cycle profile and induction of apoptosis in HL60 cells after 72 hours. (A) HL60 cells were treated with 128 nM azacitidine for 24 hours followed by 128 nM azacitidine and 133 nM CNDAC for a further 48 hours. Cells were fixed and DNA stained with propidium iodide. Single agent controls were also included. (B) HL60 cells were treated with 128 nM azacitidine for 24 hours followed by 128 nM azacitidine and 133 nM CNDAC for a further 48 hours. Cells were stained with annexin V that detected apoptotic cells and propidium iodide to detect viable cells. Single agent controls were also included. Data is the average of two samples and representative of at least two independent experiments.

FIG. 2 shows the effect of azacitidine in combination with CNDAC on the cell cycle profile and induction of apoptosis in HL60 cells after 96 hours. (A) HL60 cells were treated with 128 nM azacitidine for 24 hours followed by 128 nM azacitidine and 133 nM CNDAC for a further 72 hours. Cells were fixed and DNA stained with propidium iodide. Single agent controls were also included. (B) HL60 cells were treated with 128 nM azacitidine for 24 hours followed by 128 nM azacitidine and 133 nM CNDAC for a further 72 hours. Cells were stained with annexin V that detected apoptotic cells and propidium iodide to detect viable cells. Single agent controls were also included. Data is the average of two samples and representative of at least two independent experiments.

Figure 3:
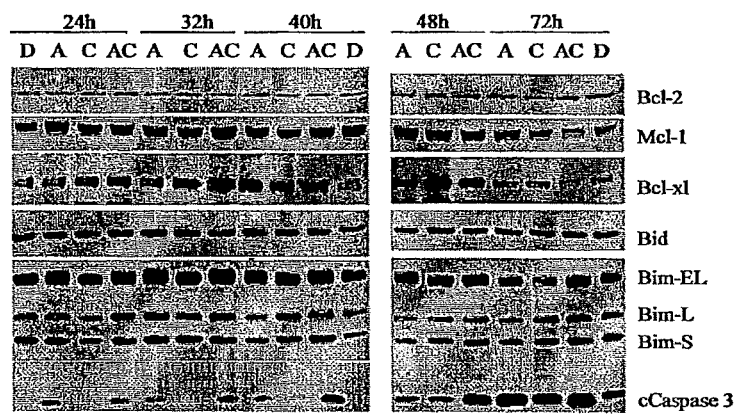

FIG. 3 shows a time course showing the effect of CNDAC and azacitidine alone or in combination on molecular events in HL60 cells. HL60 cells were treated as follows: mock treated with DMSO (D); treated with azacitidine only (0.5× IC$_{50}$: 128 nM) (A); treated with media for 24 hours followed by CNDAC (1×IC$_{50}$: 133 nM) (C); or azacitidine (128 nM) for 24 h followed by CNDAC (133 nM) (AC). Samples were collected at various times (indicated) after CNDAC addition. Cells were lysed, fractionated by SDS-PAGE, transferred to nitrocellulose and probed for cleaved PARP (a marker of apoptosis). Data is representative of two independent experiments.

EXAMPLES

Materials & Methods

Cell Lines and Reagents

MV4-11, HL60 and CEM cells were purchased from the ECACC (Salisbury, UK) ATCC. Cells were cultured at 37° C. with 5% CO$_2$ in RPMI 1640 media containing 10% fetal calf serum (FCS). Cells were kept at a density of between 0.2×10$^6$ and 1×10$^6$ cells/ml.

CNDAC was prepared in accordance with the methodology set forth in EP 535231B (Sankyo Company Limited). CYC682 (sapacitabine) was prepared in accordance with the methodology described in EP 536936B (Sankyo Company Limited). Decacitabine and Azacitidine were purchased from Sigma-Aldrich. Stock solutions of all compounds were prepared in dimethyl sulphoxide (DMSO) at 10 mM. All reagents were purchased from Sigma (Poole, UK) unless stated otherwise.

Cell Culture/Cytotoxicity Assays

In order to complete the combination studies, the cytotoxic effects of individual compounds were determined. To establish the 72 hour $IC_{50}$ for each compound, experiments were carried out in 96-well plates and the cell lines seeded at a density of 5,000/well for MV4-11 and HL60 cells and 6,000/well for CCRF-CEM cells. In each cell line, 72 h treatment $IC_{50}$ values were determined for each compound using the alamar blue assay.

A dilution series for each drug was prepared in medium. Two hours after seeding, an equal volume of each compound was added at twice the desired concentration and incubated for 72 hours. All treatments were performed in triplicate. At the end of the incubation, a 20% stock of alamar blue (Roche, Lewes, UK) was prepared in media, and an equal volume was added to each well and incubated for three hours. Absorbance was read at 544-595 nm and data was analysed (Excel Fit v4.0) to determine the $IC_{50}$ (concentration of compound that inhibited cell growth by 50%) for each compound.

CNDAC was then tested in combination with decitabine or azacitidine using three different treatment regimes: concomitant, CNDAC pre-treatment followed by methyltransferase inhibitor, and methyltransferase inhibitor pretreatment followed by CNDAC.

Calcusyn Drug Combination Protocol

Combination treatments were evaluated as follows: a cytotoxicity assay was used treating cells with two drugs at a range of concentrations and analysed using the median effect model (Chou and Talalay, 1984). For the cytotoxicity assays, treatments were either concomitant (e.g. nucleoside analogue+DMTi) or 24 hours pre-treatment of nucleoside analogue followed by 72 hours with concomitant treatment of both agents (nucleoside analogue–DMTi) and vice versa (DMTi–nucleoside analogue). Purely sequential treatments were not possible to perform with suspension cell lines. The dosing used was based around the $IC_{50}$ for 72 hours.

Since MV4-11, HL60 and CCRF-CEM cells do not adhere to 96-well plates, it was not practical to aspirate the medium from the wells, so the pre-treatment compounds were not removed during the combination experiments. For the combination analysis, 2-fold serial dilutions of each compound were used, with the concentration range of the single agents chosen so that it spanned the $IC_{50}$ value of the compound. CNDAC, decitabine and azacitidine were dissolved in DMSO prior to adding compound to media.

For the concomitant treatment, serial dilutions of CNDAC, methyltransferase inhibitor, or both drugs simultaneously were added to cells 24 h after plating, and left for 72 h at 37° C.

In the pre-treatment regimes, the first drug was added immediately after cells were plated, and left for 24 h. Fresh medium containing the second drug was then added, and incubated for 72 h. The two controls for each sequential treatment involved substituting one of the drug treatments with medium. All treatments were performed in triplicate.

After drug treatment, the cell number in each well was then estimated by incubating the cells for approximately 6 h in medium containing 10% alamar blue (Roche, Lewes, East Sussex, U.K.) and reading the absorbance at 544-595 nm. Drug interactions were analysed using the commercial software package Calcusyn, which is based on the median effect model of Chou and Talalay (Chou, T. C. & Talalay, P. (1984) Adv. Enzyme Regul. 22, 27-55. Quantatative analysis of dose-effect relationships: the combined effects of multiple drugs or enzyme inhibitors). A Combination Index (C.I.) of 1 indicated an additive drug interaction, whereas a C.I. greater than 1 was antagonistic and a score lower than 1 was synergistic. The CI value definitions are as follows: 1.45-1.2 is moderately antagonistic, 1.2-1.1 is slightly antagonistic, 1.1-0.9 is additive, 0.9-0.85 is slightly synergistic, 0.85-0.7 is moderately synergistic and 0.7-0.3 is synergistic.

Cell Cycle Analysis

Cell treatments were as follows: for single agent evaluation, HL60 cells were seeded in triplicate at 0.3×106 cells/ml in medium and were treated with 128 nM (0.5×$IC_{50}$) azacitidine or 133 nM (1×$IC_{50}$) CNDAC or DMSO only for 48 or 72 hours before harvesting for flow cytometry. For combination analysis, cells were treated with azacitidine for 24 hours followed by a further 48 or 72 hours with azacitidine and CNDAC. For controls, single agent treatments for each drug were also performed. At the end of the incubation, cells were harvested by washing twice in PBS and fixation in 70% ethanol and storage at −20° C. Prior to analysis cells were washed twice in PBS containing 1% BSA followed by staining with propidium iodide (50 µg/ml) and ribonuclease A (50 µg/ml) in PBS containing 0.1% Triton X-100 and the cell cycle profile was determined by flow cytometry.

Annexin V Staining

HL60 cells were pre-treated with 128 nM azacitidine (equivalent to 0.5×$IC_{50}$) for 24 hours followed by concomitant treatment with 128 nM azacitidine and 133 nM CNDAC (equivalent to 1×$IC_{50}$) for 48 or 72 hours. Single agent treatments were also performed as controls. After incubation cells were centrifuged at 500 g for 5 min, washed twice in PBS and once in annexin buffer (10 mM Hepes pH 7.4, 2.5 mM CaCl2, and 140 mM NaCl). Cells were resuspended at 1×10$^6$/ml and 100 µl was transferred to a 5 ml tube prior to incubation for 10 min in the dark at room temperature with 5 µl of annexin V-FITC stain (Beckton Dickinson) and 10 µl of propidium iodide [50 mg/ml]. Annexin buffer (1 ml) was added and the cells were analysed by flow cytometry. Annexin V positive cells (apoptotic) were designated on the basis of green fluorescence and propidium iodide (dead) positive cells were designated on the basis of red fluorescence.

Preparation and Analysis of Cell Lysates by Immunoblotting

Cells were seeded at 0.3×10$^8$ cells/ml in T25 flasks and treated with either DMSO, or azacitidine at 128 nM (equivalent to 0.5×$IC_{50}$) for 24 hours followed by concomitant treatment with 128 nM azacitidine and 133 nM CNDAC (equivalent to 1×$IC_{50}$) for a further 24, 36, 40, 48 and 72 hours.

Cells were harvested by centrifugation at 500 g for 5 min, washed once with ice-cold PBS and resuspended in 100 µl of lysis buffer (50 mM HEPES, pH 7.0, 20 mM NaCl, 1 mM DTT, 1× protease inhibitors, 10 mM sodium pyrophosphate, 10 mM NaF and 1 mM Na$_3$VO$_4$). All samples were lysed by sonication (2×3 s bursts using Sanyo soniprep 150 at 5 amp setting). The protein concentration of each lysate was determined using the BCA assay (Perbio Science, Northumberland, U.K.).

Lysate (30 µg) was mixed with gel loading buffer containing reducing agent and separated on 10% or 12% polyacrylamide gels using denaturing electrophoretic conditions according to manufacturers instructions (Invitrogen, Glasgow, UK). Proteins were transferred to nitrocellulose membranes (Hybond ECL, Amersham, Chalfont St. Giles, UK)

using wet electrophoretic transfer. Membranes were stained with ponceau S to confirm equal loading before blocking in 5% non-fat milk in PBS with 0.1% Tween 20 (PBSTM) for 1 hour. Membranes were incubated overnight at 4° C. with primary antibody, diluted in PBSTM. Antibodies used in this study were: cleaved PARP (Becton Dickinson). Membranes were washed in PBS and 0.1% Tween 20 (PBST) and incubated for 1 hour in PBSTM containing horseradish peroxidase-conjugated secondary antibody. Membranes were washed and incubated with ECL solution (Amersham) and exposed to X-ray film (Amersham).

Results

CNDAC and Decitabine in Combination in Haematological Cell Lines

CNDAC was tested in combination with decitabine in the AML cell lines HL60 and MV4-11, and the ALL cell line CCRF-CEM using three different treatment regimes. The Combination Index values from each drug treatment are shown for ED50, ED75 and ED90 values in Table 1 (the point on the curve where 50%, 75% and 90% of the cells have been killed). Data are the average of three independent experiments.

TABLE 1

| Cell Line | Effect | CNDAC Pretreatment | Decitabine Pretreatment | Concomitant |
|---|---|---|---|---|
| MV4-11 | ED50 | 0.95 | 1.17 | 0.79 |
| (n = 3) | ED75 | 0.71 | 0.66 | 0.88 |
|  | ED90 | 0.59 | 0.44 | 1.06 |
| HL60 | ED50 | 1.16 | 0.6 | 1.47 |
| (n = 3) | ED75 | 0.64 | 0.48 | 1.1 |
|  | ED90 | 0.68 | 0.62 | 1.86 |
| CCRF-CEM | ED50 | 0.58 | 0.94 | 1.29 |
| (n = 3) | ED75 | 0.5 | 0.68 | 0.85 |
|  | ED90 | 0.64 | 0.52 | 0.85 |

CNDAC and decitabine generated moderate to strong synergy in all three cell lines tested. CNDAC pre-treatment and decitabine pretreatment were both particularly effective treatment regimes for this combination. These results support the idea of combining CNDAC with decitabine in haematological cell lines.

CNDAC and Azacitidine in Combination in Haematological Cell Lines

CNDAC was tested in combination with azacitidine in the AML cell lines HL60 and MV4-11, and the ALL cell line CCRF-CEM using three different treatment regimes. The Combination Index values from each drug treatment are shown for ED50, ED75 and ED90 values in Table 2 (the point on the curve where 50%, 75% and 90% of the cells have been killed). Data are the average of three independent experiments.

TABLE 2

| Cell Line | Effect | CNDAC Pretreatment | Azacitidine Pretreatment | Concomitant |
|---|---|---|---|---|
| MV4-11 | ED50 | 1.23 | 1.09 | 1.13 |
| (n = 3) | ED75 | 0.95 | 1.04 | 1.03 |
|  | ED90 | 0.77 | 1.02 | 0.96 |
| HL60 | ED50 | 1.33 | 0.91 | 1.24 |
| (n = 3) | ED75 | 1.13 | 0.6 | 1.11 |
|  | ED90 | 1.03 | 0.4 | 0.99 |
| CCRF-CEM | ED50 | 0.75 | 0.76 | 1.02 |
| (n = 3) | ED75 | 0.71 | 0.61 | 1.09 |
|  | ED90 | 0.72 | 0.51 | 1.19 |

CNDAC and azacitidine induced moderate to strong synergy in all three cell lines tested. Azacitidine pretreatment generated strong synergy in HL60 and CEM cells, whereas CNDAC pre-treatment produced moderate synergy in MV4-11 and CEM cells. These results support the idea of combining CNDAC with azacitidine in haematological cell lines.

Cell Cycle Analysis

Figure 2A:
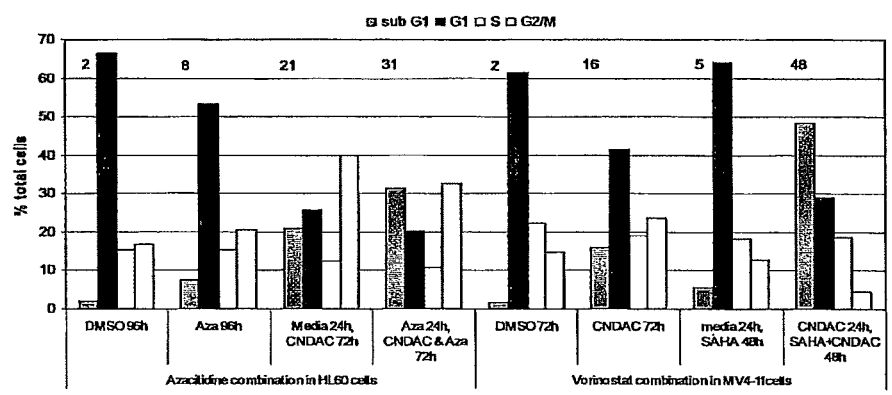

HL-60 or MV4-11 cells were treated with DMSO, CNDAC or azacitidine, as indicated in FIGS. 1A and 2A. The compound concentrations evaluated were HL-60 cells azacitidine $0.5 \times IC_{50} = 0.13$ µM; CNDAC $IC_{50} = 0.13$ µM: MV4-11 cells CNDAC $IC_{50} = 0.46$ µM. The cell cycle profiles were analysed after treatment under the indicated conditions.

Treatment with azacitidine alone caused an accumulation of cells in sub-G1, G2/M, and >G2/M seen at both 72 and 96 hours exposure (FIGS. 1A and 2A). CNDAC treatment alone caused an accumulation of cells in G2/M by 48 hours with a small induction of cells in sub-G1. The combination of agents showed a small additional increase in cells in sub-G1 with little change in the other cell cycle phases by 48 hours. By 72 hours, a more dramatic increase in sub-G1 representing 45% of the cells compared to 9% and 7% for the azacitidine and CNDAC single agent treatments respectively. Taken together these data suggest that the combination treatment causes a time dependent increase in cell death greater than either agent alone.

Annexin V Analysis

Figure 1B:
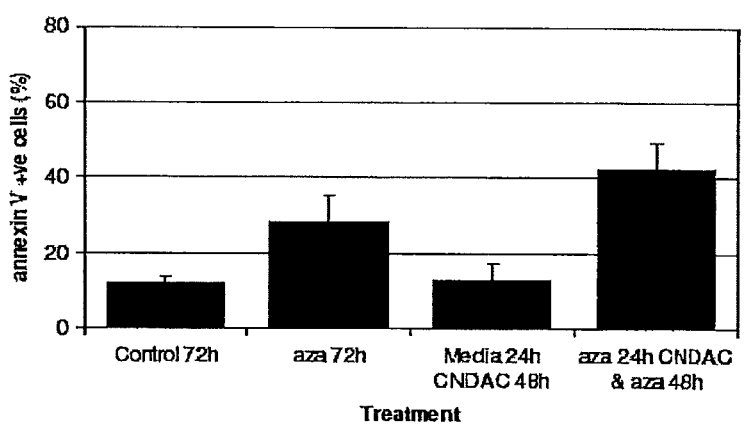
Figure 2B:
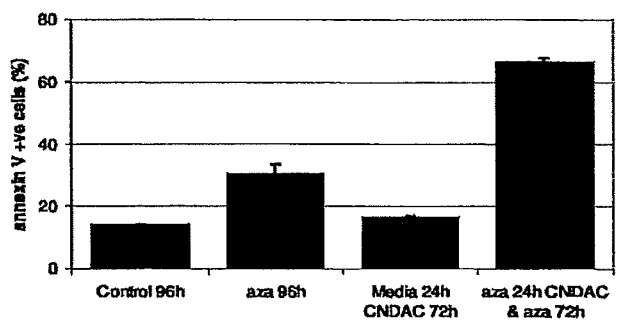

To evaluate the cell death in more detail, single agent and combination treatments of azacitidine and CNDAC in HL60s were measured by annexin V, a marker of apoptosis. Cells were exposed to azacitidine (128 nM) for a total of 96 hours. For the combination treatment after 24 hours, CNDAC (133 nM) was added for a further 72 hours in the presence of azacitidine. Single agent treatment with azacitidine caused a small increase in the proportion of apoptotic cells by 72 and 96 hours (FIGS. 1B and 2B). CNDAC alone showed little effect at either 48 or 72 hours compared to controls (FIGS. 1B and 2B). The combination of agents showed greater effects (66%) than either agent alone (azacitidine: 30.5% and CNDAC: 16.5%) with the greatest difference between single agents and the combination at the longest time point of 96 hours total treatment (FIG. 2B).

Western Blot Experiments

In order to complement the cell cycle analysis, HL60 cells treated with the single agents or with the combination were assessed for induction of cleaved PARP (a marker of apoptosis) at a range of time points (FIG. 3).

HL-60 cells were treated with DMSO, 0.13 µM azacitidine, 0.13 µM CNDAC or both agents (AC). The schedule involved 24 h azacitidine or DMSO pretreatment followed by the addition of CNDAC or DMSO for the indicated times. Cells were harvested after 48 h-96 h total treatment time. The resulting lysates (20 µg) were resolved on 12% acrylamide Bis-Tris gels, transferred to nitrocellulose membranes and probed with the antibodies shown in FIG. 3. Results showed that treatment with azacitidine alone caused a small induction in cleaved PARP at early time points. Cleaved PARP was also seen in the combination treatment. At later time points, CNDAC also induced cleaved PARP at later time points. Treatment with the combination showed greater effects on cleaved PARP than either agent alone. The results indicate that the CNDAC and azacitidine combination induces apoptosis but does not modulate Bcl-2 family proteins.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The invention claimed is:

1. A method of treating acute myelogenous leukemia, said method comprising administering to a subject, simultaneously, sequentially or separately, 1-(2-C-cyano-2-dioxy-β-D-arabino-pentofuranosyl)-N4-palmitoyl cytosine, or a metabolite thereof, and a DNA methyltransferase inhibitor selected from azacitidine, decitabine and zebularine.

2. A method according to claim 1 which comprises administering said DNA methyltransferase inhibitor to a subject prior to sequentially or separately administering 1-(2-C-cyano-2-dioxy-β-D-arabino-pentofuranosyl)-N4-palmitoyl cytosine, or a metabolite thereof, to said subject.

3. A method according to claim 1 which comprises administering 1-(2-C-cyano-2-dioxy-β-D-arabino-pentofuranosyl)-N4-palmitoyl cytosine, or a metabolite thereof, to a subject prior to sequentially or separately administering a DNA methyltransferase inhibitor to said subject.

4. A method according to any one of claims 1 to 3 wherein the DNA methyltransferase inhibitor is decitabine.

5. A method according to any one of claims 1 to 3 wherein the metabolite of 1-(2-C-cyano-2-dioxy-β-D-arabino-pentofuranosyl)-N4-palmitoyl cytosine is 1-(2-C-cyano-2-deoxy-β-D-arabino-pentafuranosyl)-cytosine.

6. A method according to any one of claims 1 to 3 wherein the DNA methyltransferase inhibitor and 1-(2-C-cyano-2-dioxy-β-D-arabino-pentofuranosyl)-N4-palmitoyl cytosine, or a metabolite thereof, are each administered in a therapeutically effective amount with respect to the individual components.

7. A method according to any one of claims 1 to 3 wherein the DNA methyltransferase inhibitor and 1-(2-C-cyano-2-dioxy-β-D-arabino-pentofuranosyl)-N4-palmitoyl cytosine, or a metabolite thereof, are each administered in a subtherapeutic amount with respect to the individual components.

8. A method according to claim 2, wherein the DNA methyltransferase inhibitor is administered at least 72 hours before the 1-(2-C-cyano-2-dioxy-β-D-arabino-pentofuranosyl)-N4-palmitoyl cytosine, or a metabolite thereof.

9. A method according to 3, wherein the 1-(2-C-cyano-2-dioxy-β-D-arabino-pentofuranosyl)-N4-palmitoyl cytosine, or a metabolite thereof is administered at least 24 hours before the DNA methyltransferase inhibitor.

10. A method according to claim 8 or 9, wherein the 1-(2-C-cyano-2-dioxy-β-D-arabino-pentofuranosyl)-N4-palmitoyl cytosine, or a metabolite thereof is administered orally.

11. A method according to claim 10, wherein the 1-(2-C-cyano-2-dioxy-β-D-arabino-pentofuranosyl)-N4-palmitoyl cytosine, or a metabolite thereof is administered in an amount of from 50 to 1000 mg per dose.

12. A method according to claim 8 or 9, wherein the DNA methyltransferase inhibitor is administered intravenously.

13. A method according to claim 12, wherein the DNA methyltransferase inhibitor is administered in an amount of between 10 to 500 mg of active ingredient per dose.

14. A method according to claim 11, wherein the DNA methyltransferase inhibitor is decitabine.

15. A method according to claim 13, wherein the DNA methyltransferase inhibitor is decitabine.

* * * * *